(12) United States Patent
Sibanda et al.

(10) Patent No.: US 12,275,697 B2
(45) Date of Patent: Apr. 15, 2025

(54) METHOD OF DEPOLYMERISING PHENOLIC POLYMERS

(71) Applicant: Stellenbosch University, Stellenbosch (ZA)

(72) Inventors: Ndumiso Sibanda, Stellenbosch (ZA); Harold Pasch, Stellenbosch (ZA); Helen Pfukwa, Stellenbosch (ZA)

(73) Assignee: Stellenbosch University, Stellenbosch (ZA)

( * ) Notice: Subject to any disclaimer, the term of this patent is extended or adjusted under 35 U.S.C. 154(b) by 721 days.

(21) Appl. No.: 17/605,769

(22) PCT Filed: Apr. 23, 2020

(86) PCT No.: PCT/IB2020/053859
§ 371 (c)(1),
(2) Date: Oct. 22, 2021

(87) PCT Pub. No.: WO2020/217209
PCT Pub. Date: Oct. 29, 2020

(65) Prior Publication Data
US 2022/0227694 A1  Jul. 21, 2022

(30) Foreign Application Priority Data
Apr. 25, 2019  (ZA) ................................. 2019/02602

(51) Int. Cl.
| | | |
|---|---|---|
| C07C 45/59 | (2006.01) | |
| C07C 27/00 | (2006.01) | |
| C07C 37/54 | (2006.01) | |
| C07C 41/01 | (2006.01) | |
| C07C 45/67 | (2006.01) | |
| C07G 1/00 | (2011.01) | |
| C08J 11/28 | (2006.01) | |
| C08L 97/00 | (2006.01) | |
| C10G 1/00 | (2006.01) | |

(52) U.S. Cl.
CPC ............ *C07C 45/673* (2013.01); *C07C 27/00* (2013.01); *C07C 37/54* (2013.01); *C07C 41/01* (2013.01); *C07C 45/59* (2013.01); *C07G 1/00* (2013.01); *C08J 11/28* (2013.01); *C08L 97/005* (2013.01); *C08J 2397/00* (2013.01); *Y02W 30/62* (2015.05)

(58) Field of Classification Search
CPC ....... C07C 45/673; C07C 37/54; C07C 41/01; C07C 27/00; C07C 45/59; C08J 2397/00; C08J 11/28; Y02W 30/62; C07G 1/00; C08L 97/005
See application file for complete search history.

(56) References Cited

U.S. PATENT DOCUMENTS

2015/0041083 A1   2/2015  Yoshikawa et al.

FOREIGN PATENT DOCUMENTS

WO    WO-2017178513 A1 * 10/2017 ............. C07C 41/01

OTHER PUBLICATIONS

Li et al., "Catalytic a-hydroxylation of ketones under CuBr2 or HBr/DMSO systems", Tetrahedron (71)(21), pp. 3247-3252 (2015).
International Search Report issued in International Application No. PCT/IB2020/053859, dated Jul. 7, 2020; 4 pages.
Sun et al., "Bright Side of Lignin Depolymerization: Toward New Platform Chemicals", Chemical Reviews (118)(2), pp. 614-678 (2018).

* cited by examiner

*Primary Examiner* — Medhanit W Bahta
(74) *Attorney, Agent, or Firm* — McNeill PLLC

(57) ABSTRACT

The invention provides a method for depolymerising a phenolic polymer, the method comprising reacting the phenolic polymer with dimethylsulphoxide (DMSO) and a hydrogen halide. The phenolic polymer may be selected from the group consisting of lignin and derivatives thereof. The hydrogen halide may be HBr. The quantity of hydrogen halide per gram of phenolic polymer may be from 30 mmoles to 70 mmoles. The quantity of DMSO per gram of phenolic polymer may be from 0.1 mole to 1 mole. The reaction may be performed at a temperature of from 100 to 120° C. The reaction may be carried out for between 10 h and 14 h. The product of the reaction may comprise vanillin.

20 Claims, 3 Drawing Sheets

METHOD OF DEPOLYMERISING PHENOLIC POLYMERS

FIELD OF THE INVENTION

This invention relates to the processing of lignin and related phenolic polymers into their constituent monomers and oligomers to provide commercially useful small molecules.

BACKGROUND TO THE INVENTION

Lignin is a class of naturally-occurring phenolic polymers that form structural materials in the supporting tissues of plants and algae. The degree of polymerisation is difficult to measure, since the material is heterogeneous. The polymers are made up of cross-linked coumaryl alcohol, coniferyl alcohol and sinapyl alcohol monomers, among other components. Lignin also contains large quantities of the commercially important compound, vanillin. Around 12,000 tons of vanillin are consumed globally per annum, 80% of which is obtained from petrochemical sources, and the remaining 20% produced from lignosulphonates.

Lignin is an attractive source of functionalised aromatic chemicals because it is relatively abundant, renewable, environmentally benign, and is currently produced in large quantities as part of agroforestry and agricultural waste. Its valorisation through depolymerisation has attracted significant attention as this offers a solution to the growing global demands for fuels and chemicals, which are currently being met through the utilisation of non-renewable petroleum feedstocks.

Structurally lignin is a complex crosslinked phenolic polymer with robust C—C and C—O bonds, which makes its depolymerisation into low molar mass aromatic monomers and oligomers a challenge. Harsh reaction conditions including extreme pH, temperature and pressure conditions, which require complicated experimental setups are thus often implemented. These extreme conditions pose severe challenges in lignin depolymerisation, which include poor selectivity and low yield. In addition, reaction media tend to be highly corrosive which poses significant waste disposal challenges.

Milder alternatives include depolymerisation using nitrobenzene, oxygen and metal oxide oxidising agents. These are widely referred to as mild oxidising agents because they can depolymerise lignin while preserving the aromatic structures of its constituent monomers to produce aldehyde functionalised aromatic compounds. While nitrobenzene can be an effective oxidant, its use often results in the formation of toxic nitrobenzene side-products such as azobenzene, 4-(phenylazo)-phenol and azoxybenzene. Nitrobenzene is also known to be carcinogenic and is therefore undesirable to handle.

Oxygen is a relatively inexpensive oxidant that is known to convert lignin to aldehydes. An advantage of using oxygen as an oxidant is that it does not require additional toxic chemicals for the reaction to proceed. However, yields tend to be low and elevated temperatures and pressure may be required to obtain satisfactory results. Furthermore, the use of oxygen without a catalyst frequently causes over oxidation, poor selectivity towards aromatic monomers and a significantly reduced level of conversion to desired products. Over oxidation leads to repolymerisation and/or the formation of undesirable gaseous compounds.

There is therefore a need for an efficient and selective method of depolymerising phenolic polymers and, more specifically, lignin in a manner which is environmentally benign and addresses some of the aforementioned challenges, at least to some extent.

The preceding discussion of the background to the invention is intended only to facilitate an understanding of the present invention. It should be appreciated that the discussion is not an acknowledgment or admission that any of the material referred to was part of the common general knowledge in the art as at the priority date of this application.

SUMMARY OF THE INVENTION

In accordance with a first aspect of this invention, there is provided a method for depolymerising a phenolic polymer, the method comprising reacting the phenolic polymer with dimethylsulphoxide (DMSO) and a hydrogen halide.

The phenolic polymer may be selected from the group consisting of lignin and derivatives thereof.

The hydrogen halide may be selected from the group consisting of HF, HCl, HBr and HI. The hydrogen halide may be HBr. The quantity of hydrogen halide per gram of phenolic polymer may be from 0.001 mmoles to 10,000 mmoles, from 0.01 mmoles to 1,000 mmoles, from 0.1 mmoles to 500 mmoles, from 1 mmole to 200 mmoles, from 10 mmoles to 100 mmoles, or from 30 mmoles to 70 mmoles.

The quantity of DMSO per gram of phenolic polymer may be from 0.001 mmoles to 10 moles, from 0.01 mmoles to 5 moles, from 0.01 mmoles to 1 mole, from 0.1 mmoles to 1 mole, from 1 mmole to 1 mole, from 10 mmoles to 1 mole, or from 0.1 mole to 1 mole.

The reaction may be performed at a temperature of from 20° C. to 200° C., from 80° C. to 150° C., or from 100° C. to 120° C. The reaction may be carried out for between 1 h and 120 h, for between 2 h and 24 h, for between 6 h and 18 h, or for between 10 h and 14 h.

The reaction may be carried out at a pressure within a range from about 101 kPa to about 500 kPa. The reaction may be carried out at atmospheric pressure.

The method may include isolating a product of the reaction. The product may be isolated at least in part by vacuum distillation. The vacuum distillation may be performed at one or more temperatures between 60° C. and 250° C., or between 100° C. and 180° C. The vacuum distillation may be performed at a pressure approximating a substantially complete vacuum, at least for practical purposes. The distillation pressure may be between 0 kPa and 50 kPa.

The product of the reaction may comprise at least one compound selected from the group consisting of monomeric and oligomeric forms of vanillin, syringaldehyde, benzaldehyde, p-hydroxybenzaldehyde, eugenol, phenol, guaiacol, phloroglucinol, 2,4-dihydroxybenzaldehyde, and aromatic hydrocarbons. The aromatic hydrocarbons may be selected from the group consisting of benzene, toluene, xylenes, and other aryl alkanes.

The product of the reaction may comprise vanillin.

In accordance with a second aspect of this invention, there is provided a method of producing an aromatic compound from a phenolic polymer, the method comprising reacting the phenolic polymer with dimethylsulphoxide (DMSO) and a hydrogen halide to form a reaction mixture, and isolating the aromatic compound from the reaction mixture.

The phenolic polymer may be selected from the group consisting of lignin and derivatives thereof.

The aromatic compound may be selected from the group consisting of monomeric and oligomeric forms of vanillin, syringaldehyde, benzaldehyde, p-hydroxybenzaldehyde, eugenol, phenol, guaiacol, phloroglucinol, 2,4-dihydroxybenzaldehyde, and aromatic hydrocarbons. The aromatic hydrocarbons may be selected from the group consisting of benzene, toluene, xylenes, and other aryl alkanes.

The aromatic compound may comprise vanillin.

The hydrogen halide may be selected from the group consisting of HF, HCl, HBr and HI. The hydrogen halide may be HBr.

The quantity of hydrogen halide per gram of phenolic polymer may be from 0.001 mmoles to 10,000 mmoles, from 0.01 mmoles to 1,000 mmoles, from 0.1 mmoles to 500 mmoles, from 1 mmole to 200 mmoles, from 10 mmoles to 100 mmoles, or from 30 mmoles to 70 mmoles.

The quantity of DMSO per gram of phenolic polymer may be from 0.001 mmoles to 10 moles, from 0.01 mmoles to 5 moles, from 0.01 mmoles to 1 mole, from 0.1 mmoles to 1 mole, from 1 mmole to 1 mole, from 10 mmoles to 1 mole, or from 0.1 mole to 1 mole.

The reaction may be performed at a temperature of from 20° C. to 200° C., from 80° C. to 150° C., or from 100° C. to 120° C. The reaction may be carried out for between 1 h and 120 h, for between 2 h and 24 h, for between 6 h and 18 h, or for between 10 h and 14 h.

The reaction may be carried out at a pressure within a range from about 101 kPa to about 500 kPa. The reaction may be carried out at atmospheric pressure.

The compound may be isolated at least in part by vacuum distillation. The vacuum distillation may be performed at one or more temperatures between 60° C. and 250° C., or between 100° C. and 180° C. The vacuum distillation may be performed at a pressure approximating a substantially complete vacuum, at least for practical purposes. The distillation pressure may be between 0 kPa and 50 kPa.

In accordance with a third aspect of this invention, there is provided a method of producing vanillin from lignin, the method comprising reacting the lignin with dimethylsulphoxide (DMSO) and a hydrogen halide to form a reaction mixture, and isolating vanillin from the reaction mixture.

The hydrogen halide may be selected from the group consisting of HF, HCl, HBr and HI. The hydrogen halide may be HBr. The quantity of hydrogen halide per gram of lignin may be from 0.001 mmole to 10,000 mmoles, from 0.01 mmoles to 1,000 mmoles, from 0.1 mmoles to 500 mmoles, from 1 mmole to 200 mmoles, from 10 mmoles to 100 mmoles, or from 30 mmoles to 70 mmoles.

The quantity of DMSO per gram of lignin may be from 0.001 mmoles to 10 moles, from 0.01 mmoles to 5 moles, from 0.01 mmoles to 1 mole, from 0.1 mmoles to 1 mole, from 1 mmole to 1 mole, from 10 mmoles to 1 mole, or from 0.1 mole to 1 mole.

The reaction may be performed at a temperature of from 20° C. to 200° C., from 80° C. to 150° C., or from 100° C. to 120° C. The reaction may be carried out for between 1 h and 120 h, for between 2 h and 24 h, for between 6 h and 18 h, or for between 10 h and 14 h.

The reaction may be carried out at a pressure within a range from about 101 kPa to about 500 kPa. The reaction may be carried out at atmospheric pressure.

The vanillin may be isolated at least in part by vacuum distillation. The vacuum distillation may be performed at a temperature of between 170° C. and 200° C., or between 175° C. and 185° C. The vacuum distillation may be performed at a pressure approximating a substantially complete vacuum, at least for practical purposes. The distillation pressure may be between 0 kPa and 50 kPa.

Certain modes of performing the invention will now be described, by way of example only, with reference to the accompanying figures.

DETAILED DESCRIPTION WITH REFERENCE TO THE FIGURES

Figure 1:
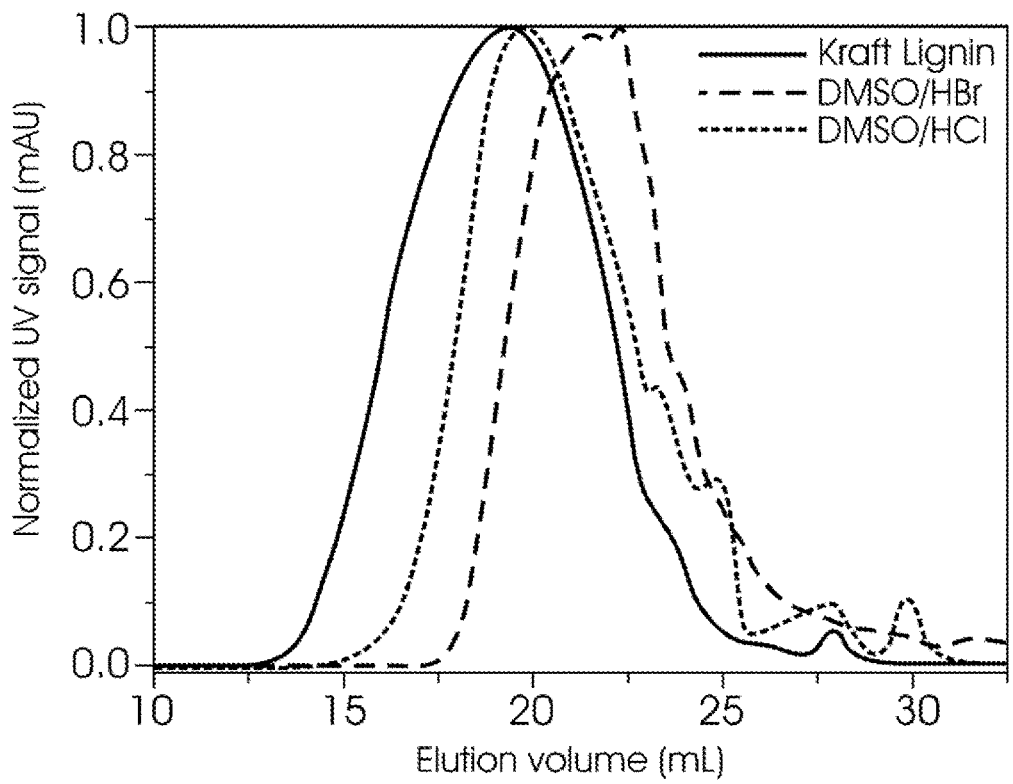
FIG. 1 is a size exclusion chromatography (SEC) elution profile (elugram) showing depolymerisation products of Kraft lignin resulting from reaction with DMSO/HBr and DMSO/HCl.

The invention provides a method of depolymerising a phenolic polymer, such as lignin, into its constituent monomers and/or oligomers under mild oxidising conditions using a combination of DMSO and hydrogen halide. The method provides a means of obtaining these compounds from lignocellulosic biomass, technical lignins, lignin residue, agricultural waste and/or agroforestry waste, instead of from petrochemicals from which they are traditionally obtained.

The term "lignin" as used herein refers to any lignin or lignin derivative including but not limited to technical lignins such as kraft lignin, softwood kraft lignin, hardwood kraft lignin, Brauns' lignin, cellulolytic enzyme lignin, dioxane acidolysis lignin, Klason lignin, milled wood lignin, periodate lignin, lignosulphates, lignosulphonates, organosolv lignin, steam explosion lignin, lignocellulosic biomass, and lignin residue. It also refers to any substances made in whole or in part from lignin or subunits of lignin.

As used herein, the term "lignosulphonate" refers to a sulphonated lignin, which is a water-soluble anionic polyelectrolyte polymer typically produced as a byproduct of the sulphite process used in wood pulp manufacturing. Sulphite pulping removes lignin from wood particles to form lignosulphonate and substantially pure cellulose wood pulp.

"Kraft lignin" refers to lignin produced as a byproduct of the Kraft process for producing wood pulp. The Kraft process involves treating wood chips with a hot mixture of water, sodium hydroxide (NaOH) and sodium sulphide ($Na_2S$), which breaks the bonds that link lignin, hemicellulose and cellulose.

"Lignin residue" refers to lignin that is produced as a by-product from biomass, agricultural and/or agroforestry waste processing or any lignin depolymerisation process. The production of the lignin residue may include but is not limited to enzymatic, oxidative or acid/base catalyzed protocols.

The term "oligomer" will be understood to refer to a molecule of intermediate relative molar mass, the structure of which essentially comprises a small plurality of units derived, actually or conceptually, from molecules of lower relative molar mass. A molecule is regarded as having an intermediate relative molar mass if it has properties which do vary significantly with the removal of one or a few of the units. If a part or the whole of the molecule has an intermediate relative molar mass and essentially comprises a small plurality of units derived, actually or conceptually, from molecules of lower relative molar mass, it may be described as oligomeric, or as an oligomer. An oligomer is essentially a molecular complex that includes a limited number of monomer units, such as from 2 to 8 or from 2 to 5 monomer units. In the case of lignin, these monomers tend to be derivatives of phenol. The molar mass of these oligomers may be less than 2000 g/mol as determined from techniques usually used in the field, e.g. size exclusion chromatography.

The term "phenolic" is understood to refer to molecules which include phenol or a derivative thereof in their molecular structure, or which are derived from phenol-containing molecules. Examples of phenolic compounds include lignin, vanillin, syringaldehyde, p-hydroxybenzaldehyde, eugenol, phenol, guaiacol, phloroglucinol and 2,4-dihydroxybenzaldehyde.

Throughout this specification, certain embodiments are described in a range format. It should be understood that the description in range format should not be construed as an inflexible limitation on the scope of the disclosed ranges. Accordingly, ranges are to be interpreted as disclosing all possible sub-ranges and individual numerical values within the range, and to be inclusive of the stated lower and upper bounds of the range. A description of a range of from 1 to 6 should be considered as specifically disclosing sub-ranges such as from 1 to 3, from 1 to 4, from 1 to 5, from 2 to 4, from 2 to 6, from 3 to 6, etc., as well as individual numbers within that range, i.e. 1, 2, 3, 4, 5, and 6. A description of a range of temperatures between 170° C. and 200° C. should be considered as specifically disclosing the upper and lower bounding temperatures (i.e. 170° C. and 200° C.) as well as all possible sub-ranges and individual numerical values within that range.

Throughout the specification and claims unless the context requires otherwise the word "comprise" or variations such as "comprises" or "comprising" will be understood to imply the inclusion of a stated integer or group of integers but not the exclusion of any other integer or group of integers.

The method includes reacting the phenolic polymer with dimethylsulphoxide (DMSO) and a hydrogen halide. The polymer, DMSO and hydrogen halide form a reaction mixture which is typically heated for a defined period of time at a specific temperature or temperature range. The DMSO acts as a mild oxidising agent and solvent, while the hydrogen halide acts as a Brønsted acid catalyst for the reaction. There are several advantages of using this DMSO-based oxidation system which include (1) DMSO is a selective reagent, (2) it is a mild reagent, (3) there is no over oxidation of primary alcohols to carboxylic acids i.e. the oxidation of primary alcohols gives aldehydes, (4) it is a very good solvent for lignin, (5) it is commercially available as well as relatively inexpensive, and (6) it is relatively non-toxic and environmentally friendly in comparison to some other metal-based oxidation systems.

The quantity of DMSO per gram of phenolic polymer in the reaction can be from 0.001 mmoles to 10 moles, from 0.01 mmoles to 5 moles, from 0.01 mmoles to 1 mole, from 0.1 mmoles to 1 mole, from 1 mmole to 1 mole, from 10 mmoles to 1 mole, or from 0.1 mole to 1 mole.

The hydrogen halide can be selected from hydrogen fluoride (HF), hydrogen chloride (HCl), hydrogen bromide (HBr) and hydrogen iodide (HI). In some embodiments, the hydrogen halide is HBr. The quantity of the hydrogen halide per gram of phenolic polymer in the reaction can be from 0.001 mmoles to 10,000 mmoles, from 0.01 mmoles to 1,000 mmoles, from 0.1 mmoles to 500 mmoles, from 1 mmole to 200 mmoles, from 10 mmoles to 100 mmoles, or from 30 mmoles to 70 mmoles.

The reaction is typically carried out at a moderately elevated temperature and can be performed at a temperature of from 20° C. to 200° C., from 50° C. to 150° C., from 80° C. to 140° C., or from 100° C. to 120° C. The length of the reaction can vary depending on the temperature. Longer reaction times at higher temperatures result in greater conversion but can cause an increase in side product formation. Typically the reaction can be carried out for between 1 h and 120 h, for between 2 h and 48 h, for between 6 h and 24 h, or for between 10 h and 14 h. The pressure at which the depolymerisation is carried out may be in a range of between 101 kPa and 500 kPa. Said pressure may be atmospheric pressure.

The method may further include isolating one or more products of the reaction from the reaction mixture after the reaction is complete. The product may be a monomeric or oligomeric aromatic phenolic compound, such as vanillin, syringaldehyde, benzaldehyde, p-hydroxybenzaldehyde, eugenol, phenol, guaiacol or 2,4-dihydroxybenzaldehyde. The one or more products of the reaction may also comprise an aromatic hydrocarbon, e.g. benzene, toluene or xylenes. The product or products may be isolated by solvent extraction, chromatography (e.g. size exclusion chromatography, column chromatography, ion exchange chromatography, reversed phase chromatography, or normal phase chromatography), and/or distillation (e.g. simple distillation, fractional distillation or vacuum distillation).

Since the boiling point of the monomers and/or oligomers of phenolic polymers is relatively high (e.g. >180° C. for phenol), the product is preferably isolated at least in part by vacuum distillation so that the distillation temperature can be reduced. Vacuum distillation refers to distillation of a liquid under reduced pressure enabling it to boil at a lower temperature than at atmospheric pressure. This technique is capable of separating different compounds based on differences in their boiling points and can be used when the boiling point of a desired compound is difficult to achieve or will cause the compound to decompose. Lower distillation temperatures reduce the likelihood of degradation of the product. The vacuum distillation can be performed at one or more different temperatures, depending on how many products are isolated. Products having different boiling points can be collected at different temperatures, under vacuum (at approximately 0 kPa for example).

While the vacuum distillation can be performed at any suitable temperature, it is preferably done at a temperature of between 60° C. and 250° C., or between 100° C. and 180° C. For example, the product(s) can be distilled under vacuum at 100° C. to 130° C., 140° C. to 150° C., approximately 160° C. and/or approximately 180° C., and at a pressure ranging from approximately 0 kPa to 50 kPa. Syringaldehyde and benzaldehyde can be collected at between 140° C. and 150° C.; eugenol can be collected at between 155° C. and 165° C., preferably at about 160° C.; and vanillin and/or p-hydroxybenzaldehyde can be collected at between 170° C. and 200° C., preferably between 175° C.

and 185° C., or at about 180° C. Phloroglucinol, 2,4-dihydroxybenzaldehyde, phenol and guaiacol can be collected from an undistilled, high boiling point fraction of the reaction product. Aromatic hydrocarbons such as benzene, toluene, xylenes and aryl alkanes, can also be collected from the undistilled high boiling point fraction.

The phenolic polymer, DMSO or hydrogen halide may be at least partially dissolved in a solvent. The solvent may be selected from dimethyl acetamide (DMAC), dimethyl formamide (DMF), n-alkyl pyrrolidone (such as N-methyl-2-pyrrolidone (NMP)), acetone, acetonitrile, tetrahydrofuran, water, ethyl acetate, alkyl alcohols (such as methanol and ethanol), 2-pyrrolidone, ethylene carbonate, propylene carbonate, γ-butyrolactone, caprolactam, γ-valerolactone, dimethylbenzamide, diethylbenzamide, other dialkylacetamides, N-methyl-2-piperidone, 2-piperidone, other N-alkyl piperidones, the aforementioned solvents in combination with water e.g. water/methanol, water/DMSO, water/acetonitrile, water/THF in varying quantities and varying ratios.

The invention will now be described in further detail by way of the following non-limiting examples.

EXAMPLES

Materials

Alkaline lignin (Kraft lignin) with low sulphonate content and lignosulphonate were dried overnight in an oven at 105° C. to a constant mass, before depolymerisation. Dimethyl sulphoxide (DMSO, HPLC grade, 99.7%, Sigma-Aldrich, Poznan, Poland), hydrogen bromide (HBr, 48%, Sigma-Aldrich, St. Louis, USA), and hydrochloric acid (HCl, 32%, Merck, Darmstadt, Germany) were used as received.

Oxidative Depolymerisation of Lignin

Example I

HBr as Catalyst:

Kraft lignin (0.2 g) was dissolved in DMSO (8 mL, $1.13 \times 10^{-1}$ moles) in a round bottom flask, and a catalytic amount of HBr (1 mL, $8.8 \times 10^{-3}$ moles) was added to the reaction mixture. The reaction flask was immersed in an oil bath set at 110° C., and the reaction mixture heated for 12 hrs. The reaction was then stopped by cooling to room temperature. The reaction was repeated using a lignosulphonate instead of Kraft lignin following the same procedure and under the same experimental conditions.

Example II

HCl as Catalyst:

Kraft lignin (0.2 g) was dissolved in DMSO (8 mL, $1.13 \times 10^{-1}$ moles) in a round bottom flask, and a catalytic amount of HCl (1 mL, $1.06 \times 10^{-2}$ moles) was added to the reaction mixture. The reaction flask was immersed into an oil bath thermostated at 110° C., and the reaction mixture heated for 12 hrs. The reaction was then stopped by cooling to room temperature.

The extent of depolymerisation was determined gravimetrically using the equations below:

% of native lignin=(Weight of precipitated lignin/Initial weight of lignin)×100%

Conversion=100−% native lignin where Initial weight of lignin is the mass of lignin before the depolymerisation reaction and Weight of precipitated lignin is the native lignin, which was precipitated from water from the product mixture and isolated through centrifugation. The supernatant was decanted and residual water removed under vacuum.

Size exclusion chromatography (SEC)

An Agilent 1200 HPLC instrument (Agilent Technologies, Waldbronn, Germany) was used, comprising the following: autosampler, on-line degasser, quaternary pump unit and a thermostated column compartment set to 55° C. The detector used was an Agilent ultraviolet (UV) detector at a wavelength of 277 nm. Two 10 μm PSS GRAM columns (PSS Polymer Standards Service GmbH, Mainz, Germany) (with polyester copolymer as a stationary phase) with porosities of 100 Å and 1000 Å and a 10 μm guard column were used. The sample solvent and mobile phase was DMSO/H$_2$O/LiBr (90:10:0.05 M respectively), and a flow-rate of 0.4 mL/min was used. Calibration was carried out using narrow poly(styrene sulphonate) sodium salt (PSS Polymer Standards Service GmbH, Mainz, Germany) with peak maximum molar masses ($M_p$) ranging from 891 to 1 000 000 g/mol. PSS WinGPC Unichrom software (8.2) was used to acquire and process the data.

An Agilent 1100 refractive index (RI) detector was later added to the HPLC instrument because pullulan standards (PSS Polymer Standards Service GmbH, Mainz, Germany, having a peak molar mass ($M_p$) between 342 and 1 220 000 g/mol) which did not have UV chromophore were used to calibrate the columns. The pullulan standards were used because the lignosulphonate and most depolymerised products were eluting after the lowest poly(styrene sulphonate) sodium salt standard with peak molar mass ($M_p$) of 891 g/mol. All molar mass values are, therefore, calculated and reported as pullulan equivalents.

SEC analysis was used to investigate the oxidative depolymerisation of lignin. The following parameters that ensure optimum separation were considered: mobile phase composition, choice of stationary phase, operating temperature, and use of an electrolyte to disrupt non-covalent polymer-polymer and polymer-stationary phase interactions.

When solubility studies were carried out, it was found that Kraft lignin (with low sulphonate content) and lignosulphonate (with high sulphonate content) together with their respective products of depolymerisation, dissolved completely in a DMSO/H$_2$O/LiBr (90:10% (v/v):0.05M) mobile phase, without the need for derivatisation. PSS GRAM columns were selected due to their compatibility with the mobile phase and polymer. Porosities of 100 Å and 1000 Å were selected for the columns in order to cover a wider separation range taking into account that depolymerisation of lignin would result in low molar mass compounds. All SEC measurements were carried out at a UV wavelength of 277 nm.

FIG. 1 shows a SEC elugram of native lignin and the crude products of oxidative depolymerisation from Examples I and II, using DMSO/HBr and DMSO/HCl systems, respectively. The shift towards higher elution volume following the reactions is a confirmation of the success of the oxidative depolymerisation reaction, which is corroborated by a clear decrease in molar mass as shown in Table 1 ($M_w$ decreased from 14650 g/mol for the lignin, to 2180 g/mol for the product of depolymerisation using HBr as catalyst).

A comparison of the molar masses of the products of the DMSO/HBr and DMSO/HCl reactions shows that DMSO/HBr is a more effective system for depolymerising lignin than DMSO/HCl. The molar mass dispersity for the two systems decreased significantly after depolymerisation.

Table 1 below provides a summary of the respective molar masses of the reaction products.

TABLE 1

Molar mass information on Kraft lignin and depolymerised product of oxidative depolymerisation by DMSO/HBr and MSO/HCl.

| | $^a$ $M_n$ (g/mol) | $^b$ $M_w$ (g/mol) | $^c$ $M_p$ (g/mol) | $^d$ Đ |
|---|---|---|---|---|
| Kraft lignin | 3750 | 14 650 | 9630 | 3.9 |
| Depolymerisation by DMSO/HBr | 1400 | 2180 | 1550 | 1.6 |
| Depolymerisation by DMSO/HCl | 2830 | 6340 | 5230 | 2.2 |

$^a$ Number average molar mass ($M_n$),
$^b$ weight average molar mass ($M_w$),
$^c$ peak molar mass ($M_p$),
$^d$ molar mass dispersity (Đ), measured using the SEC method described previously.

Example III

Table 2 tabulates the percentage conversions obtained for the DMSO/HBr system with lignin. The DMSO/HBr oxidation was also performed at a scaled-up quantity of 10 g lignin and showed a similar conversion rate to the 0.2 g reaction, indicating that the reaction is scalable.

TABLE 2

Percentage conversion of oxidative depolymerisation of lignin using DMSO/HBr.

| | Percentage Conversion |
|---|---|
| DMSO/HBr (0.2 g) | 46.3% |
| DMSO/HBr (10 g) | 44.5% |

Example IV

Oxidative Depolymerisation of Lignosulphonate by DMSO/HBr

Figure 2:
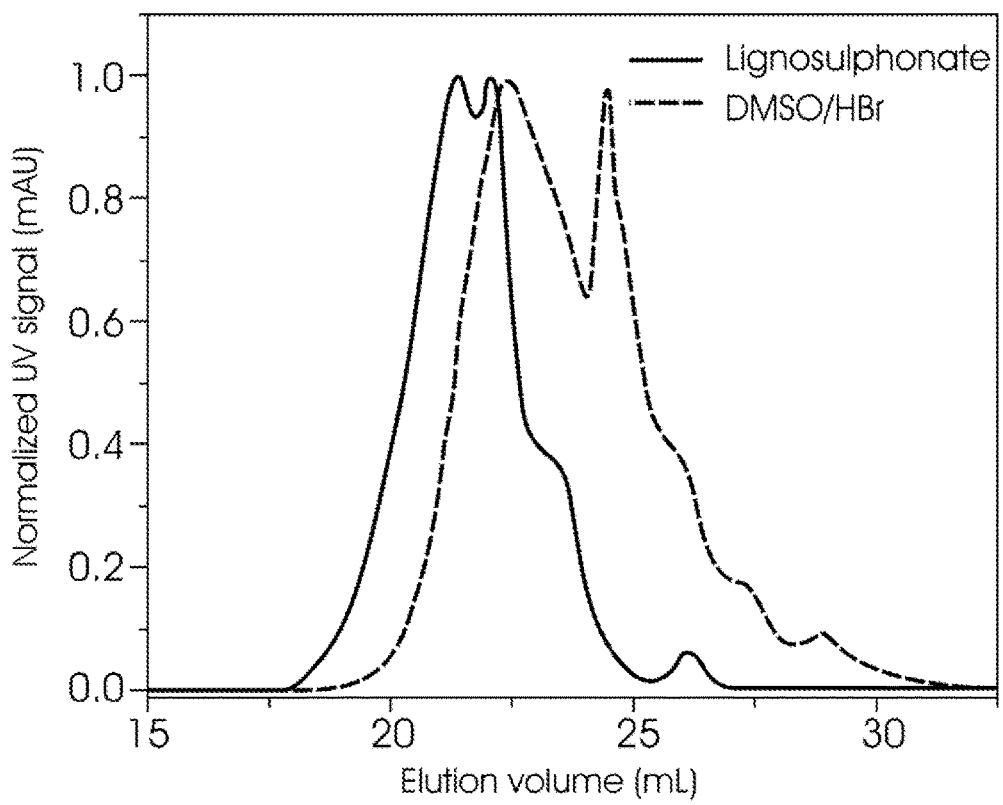
FIG. 2 is a size exclusion chromatography (SEC) elution profile (elugram) showing untreated lignosulphonate and products of oxidative depolymerisation of lignosulphonate with DMSO/HBr.

The oxidative depolymerisation reaction was applied to a sample of lignosulphonate and the resulting SEC elution profile of the reaction product is illustrated in FIG. 2. The decrease in elution volumes and $M_w$ can be seen from the graph. The $M_w$ values of the reactant and product are illustrated in Table 3 below and show that the weight average molar mass decreased from 4020 g/mol for lignosulphonate to 1080 g/mol for the depolymerisation product.

TABLE 3

Molar mass information of lignosulphonate starting material (s.m.) and product resulting from oxidative depolymerisation with DMSO/HBr.

| | $^a$ $M_n$ (g/mol) | $^b$ $M_w$ (g/mol) | $^c$ $M_p$ (g/mol) | $^d$ Đ |
|---|---|---|---|---|
| Lignosulphonate s.m. | 1550 | 4020 | 1220 | 2.6 |
| Lignosulphonate depolymerisation product (DMSO/HBr) | 900 | 1080 | 950 | 1.2 |

$^a$ Number average molar mass ($M_n$),
$^b$ weight average molar mass ($M_w$),
$^c$ peak molar mass ($M_p$),
$^d$ molar mass dispersity (Đ)

Analysis of Reaction Products

In one example of the described DMSO/HBr reaction, the pH of the starting reaction and of the resultant crude product mixture were measured. The starting reagents had a pH of approximately 4 whilst the products of the reaction had a pH of between 6 and 8.

Gas chromatography-mass spectrometry (GC-MS) using electron impact (EI) ionisation was used to identify products of the oxidative depolymerisation reaction of lignin with DMSO/HBr of Example 1. These compounds are presented in Table 4 below:

TABLE 4

Summary of compounds identified by GC-MS in the reaction mixture.

| Product | Retention time (min) | Characteristic ions (m/z) |
|---|---|---|
| P-xylene (G1) | 5.06 | 43, 61, 91, 106 |
| Propyl-toluene (1-methyl-4-propyl-benzene) (G 2) | 5.26 | 61, 96, 105, 134 |
| Benzeneethanol (2-phenylethanol) (G3) | 5.55 | 91, 106, 122 |
| (E)-1,7-bis(4-hydroxy-3-methyl-phenyl)hept-4-en-3-one (G4) | 5.73 | 73, 267, 355, 356 |
| 4-(pentyloxy)benzaldehyde (G5) | 6.06 | 42, 121, 123, 192 |
| 4-phenyl-2-buten-1-al (G6) | 6.12 | 45, 87, 146 |
| Vanillin acetate ((4-formyl-2-methoxyphenyl) acetate) (G7) | 6.40 | 43, 107, 152 194 |
| 4-methylbenzaldehyde (G8) | 6.54 | 63, 75, 119, 120 |
| 2,4-dimethylphenol (G9) | 7.26 | 45, 62, 107, 122 |
| Acetophenone (1-phenylethanone) (G10) | 7.50 | 43, 61, 90, 120 |
| 3,5-dimethoxy-4-hydroxycinnamaldehyde ((E)-3-(4-hydroxy-3,5-dimethoxyphenyl)prop-2-enal) (G11) | 7.83 | 43, 61, 78, 126, 151, 208 |
| p-hydroxybenzaldehyde (G12) | 10.38 | 39, 43, 79, 93, 122 |
| 2,6'-dimethoxyacetophenone (G13) | 10.50 | 45, 65, 119, 120 |
| 2-(3,4-dihydroxyphenyl)acetic acid (G14) | 11.10 | 51, 63, 77, 123, 168 |
| 4'-hydroxyacetophenone (G15) | 12.32 | 63, 78, 94, 136 |
| Acetosyringone (1-(4-hydroxy-3,5-dimethoxyphenyl)ethanone) (G16) | 12.83 | 63, 81, 110, 126, 196 |
| 4-hydroxybenzoic acid (G17) | 13.11 | 47, 77, 93, 121, 138 |
| 3-methoxycatechol (3-methylbenzene-1,2-diol) (G18) | 14.09 | 79, 123, 140 |
| 3,4-dihydroxybenzaldehyde (G19) | 14.26 | 79, 109, 138 |
| Dihydroxyacetophenone (2,2-dihydroxy-1-phenylethanone) (G20) | 15.55 | 77, 105, 122, 152 |
| Vanillin (4-hydroxy-3-methoxybenzaldehyde) (G21) | 16.40 | 81, 109, 151, 152 |
| Isovanillic acid (3-hydroxy-4-methoxybenzoic acid) (G22) | 16.48 | 121, 151, 153, 168 |
| trans-4,4'-dimethoxy-beta-methyl-chalcone (G23) | 18.06 | 79, 239, 267, 282 |
| Syringaldehyde (4-hydroxy-3,5-dimethoxybenzaldehyde) (G24) | 19.06 | 45, 88, 181, 182 |
| (2,4-dihydroxyphenyl)-(4-hydroxyphenyl)methanone (G25) | 20.31 | 51, 79, 135, 230 |

Gas chromatography-mass spectrometry (GC-MS) and electrospray ionisation-mass spectrometry (ESI-MS) analyses were also performed to identify the products of the lignosulphonate depolymerisation reaction from Example IV. The products included guaiacol (E2), hydroxybenzaldehyde (E1), 1-(2-hydroxyphenyl)ethanone (E3), 2-methoxy-4-methylphenol (4-methylguaiacol) (E4), (E)-3-(4-hydroxyphenyl)prop-2-enal (4-hydroxycinnamaldehyde (E8)), 4-hydroxy-3-methoxybenzaldehyde (vanillin) (E10), 3-phenylpropanal (E11), 3-methoxybenzaldehyde (E12), (E)-3-(4-hydroxy-3-methoxyphenyl)prop-2-enal (coniferaldehyde) (E14), 2-formyl-5-methoxyphenyl acetate (E16), ethyl 2-(4-hydroxy-3-methoxyphenyl)acetate (ethyl homovanillate) (E17), (Z)-3-(3,4,5-trimethoxyphenyl)prop-2-enal (3,5-trimethoxycinnamaldehyde) (E19), 2-hydroxy-4,4'-diethoxybenzophenone (E23), ethyl 4-methoxyphenyl isophthalate (E24) and 1-(4-(1-(4-hydroxy-3-methoxyphenyl)prop-1-en-2-yloxy)-3,5-dimethoxyphenyl)ethanone (E25). The chemical structures of these compounds as well as their characteristic m/z ratios and theoretical masses are shown in Table 5 below.

TABLE 5

Summary of compounds identified by ESI-MS in the lignosulphonate, DMSO and HBr product mixture.

| $^a$m/z | $^b$M (g/mol) | Structure |
|---|---|---|
| 123, 145 | 122 | p-hydroxybenzaldehyde (E1) |
| 125 | 124 | 2-methoxyphenol (guaiacol) (E2) |
| 136, 137 | 136 | 1-(2-hydroxyphenyl)ethanone (2-hydroxyacetophenone) (E3) |
| 138 | 138 | 2-methoxy-4-methylphenol (4-methyl guaiacol) (E4) |
| 141 | 140 | 3-methoxybenzene-1,2-diol (3-methoxycatechol) (E5) |
| 143 (M + Na$^+$) | 120 | 4-methylbenzaldehyde (E6) |
| 147 | 146 | 4-phenyl-2-buten-1-al (E7) |
| 149 | 148 | (E)-3-(4-hydroxyphenyl)prop-2-enal (4-hydroxycinnamaldehyde) (E8) |
| 150 | 150 | 4-ethenyl-2-methoxyphenol (vinylguaiacol) (E9) |
| 152, 153, 175 | 152 | 4-hydroxy-3-methoxybenzaldehyde (vanillin) (E10) |
| 157 (M + Na$^+$) | 134 | 3-phenylpropanal (E11) |
| 165 | 164 | 2-methoxy-4-prop-2-enylphenol (eugenol) (E13) |
| 178, 179 | 178 | (E)-3-(4-hydroxy-3-methoxyphenyl)prop-2-enal (coniferaldehyde) (E14) |

TABLE 5-continued

Summary of compounds identified by ESI-MS in the lignosulphonate, DMSO and HBr product mixture.

| $^a$m/z | $^b$M (g/mol) | Structure |
|---|---|---|
| 181 | 180 | 4-[(E)-3-hydroxyprop-1-enyl]-2-methoxyphenol (coniferyl alcohol) (E15) |
| 195 | 194 | (4-formyl-2-methoxyphenyl) acetate (E16) |
| 211 | 210 | ethyl 2-(4-hydroxy-3-methoxyphenyl)acetate (ethyl homovanillate) (E17) |
| 215 | 214 | bis(4-hydroxyphenyl)methanone (E18) |
| 223 | 222 | (Z)-3-(3,4,5-trimethoxyphenyl)prop-2-enal (3,5-trimethoxycinnamaldehyde) (E19) |
| 227 | 226 | ethyl 4-hydroxy-3,5-dimethoxybenzoate (ethyl syringate) (E20) |
| 245 | 244 | 4-(hydroxy(4-hydroxyphenyl)methoxy)benzaldehyde (E21) |
| 261 | 260 | 4-(1-hydroxy-2-(2-methoxyphenoxy)ethyl)phenol (E22) |
| 287 | 286 | 2-Hydroxy-4,4'-diethoxybenzophenone (E23) |
| 301 | 300 | ethyl 4-methoxyphenyl isophthalate (E24) |

TABLE 5-continued

Summary of compounds identified by ESI-MS in the lignosulphonate, DMSO and HBr product mixture.

| $^a$m/z | $^b$M (g/mol) | Structure |
|---|---|---|
| 359 | 358 | 1-(4-(1-(4-hydroxy-3-methoxyphenyl)prop-1-en-2-yloxy)-3,5-dimethoxyphenyl)ethanone (E25) |
| 419 | 418 | 4-(4-(4-hydroxy-3,5-dimethoxyphenyl)-hexahydrofuro[3,4-c]furan-1-yl)-2-methoxy-6-methylphenol (E26) |
| 537 | 536 | 4-(3-hydroxy-1,2-bis(4-((E)-3-hydroxyprop-1-enyl)-2-methoxyphenoxy)propyl)-2-methoxyphenol (E27) |
| 611 | 610 | 1-(4-(3-hydroxy-1,2-bis(4-((E)-3-hydroxyprop-1-enyl)-2-methoxyphenoxy)propyl)-2-methoxyphenoxy)propane-1,3-diol (E28) |

$^a$m/z observed, [M + H]⁺ or [M + Na]⁺ or [M + K]⁺, Theoretical mass (M) $^b$. The letter E before a number is used to denote structures obtained from ESI-MS A summary of the products and their relative abundances are provided in Table 6 below.

TABLE 6

Comparison of relative abundances of monomer products obtained from lignin and lignosulphonate by oxidative depolymerisation as determined by GC-MS (RT = retention time in minutes on column). Example V

| | Lignin | | Lignosulphonate | |
|---|---|---|---|---|
| | RT | % Abundance | RT | % Abundance |
| Furfural | 8.71 | 9.60 | 8.72 | 4.3 |
| 5-Methyl furfural | 9.70 | 4.01 | 9.70 | 1.5 |
| Guaiacol | 11.92 | 0.59 | 11.92 | 0.24 |
| Methyl guaiacol | 12.67 | 0.11 | 12.59 | 0.06 |
| Ethyl guaiacol | 13.09 | 0.03 | 13.08 | 0.007 |
| m-Cresol | 13.40 | 0.014 | 13.41 | 0.002 |
| Eugenol | 13.98 | 0.04 | 13.98 | 0.007 |
| 5-Hydroxymethyl furfural | 16.02 | 1.42 | 16.02 | 0.19 |
| Vanillin | 16.42 | 44.1 | 16.42 | 59.0 |
| Syringaldehyde | 19.06 | 40.0 | 19.06 | 34.3 |
| Coniferaldehyde | 21.45 | 0.01 | 21.45 | 0.003 |

Influence of HBr Concentration

The influence of the concentration of HBr catalyst used was investigated by varying the amount of catalyst added as follows: 0.001 moles, 0.003 moles, 0.009 moles, 0.020 moles, 0.050 moles and 0.100 moles, with the other reaction parameters having been kept constant as in Example 1, i.e. the amounts of DMSO and lignin, and the reaction time and temperature. Table 7 tabulates a selection of the parameters and conditions used for the study.

TABLE 7

Experimental parameters and conditions for study on
influence of varying HBr catalyst concentration.

| Reaction | Reagents | Temperature (° C.) |
|---|---|---|
| 1 | Kraft lignin (2 g), DMSO (1.13 × $10^{-1}$ moles), HBr (0.001 moles) | 110 |
| 2 | Kraft lignin (2 g), DMSO (1.13 × $10^{-1}$ moles), HBr (0.003 moles) | 110 |
| 3 | Kraft lignin (2 g), DMSO (1.13 × $10^{-1}$ moles), HBr (0.009 moles) | 110 |
| 4 | Kraft lignin (2 g), DMSO (1.13 × $10^{-1}$ moles), HBr (0.020 moles) | 110 |
| 5 | Kraft lignin (2 g), DMSO (1.13 × $10^{-1}$ moles), HBr (0.050 moles) | 110 |
| 6 | Kraft lignin (2 g), DMSO (1.13 × $10^{-1}$ moles), HBr (0.100 moles) | 110 |

Size exclusion chromatography (SEC) was used to monitor the success of the depolymerisation reaction. A shift from lower to higher elution volumes would indicate that the chemical linkages in the high molar mass lignin were cleaved, and lower molar mass oligomeric and monomeric species formed. On the other hand, a shift towards lower elution volumes would indicate that unwanted recombination (condensation) reactions had occurred.

Figure 3:
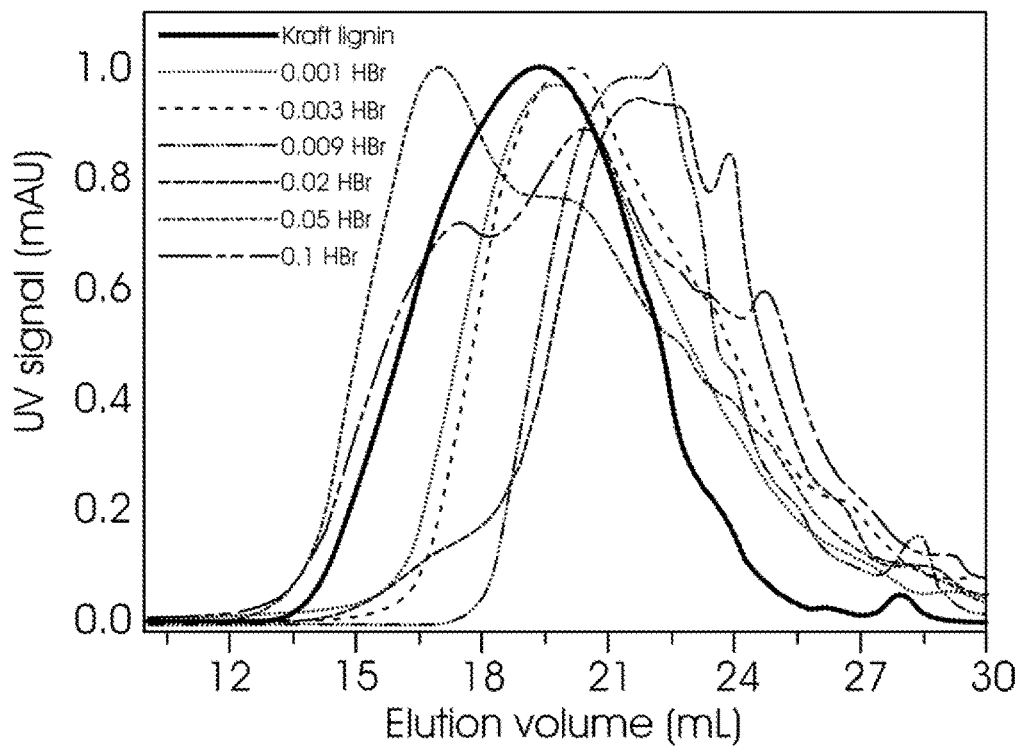
FIG. 3 is a series of SEC elution profiles illustrating the influence of varying HBr concentration.

FIG. 3 shows the SEC elugrams that were obtained. Although the system was not calibrated to give exact molar mass information, it is evident that HBr quantities of 0.001 and 0.003 resulted in a slight shift towards lower molar masses compared to the method where 0.009 moles of HBr were used. Increasing the amount of HBr to 0.020 moles gave a shift in elution volume comparable to that obtained for the sample with 0.009 moles of HBr, but the presence of recombination side reactions became apparent between 15 and 18 mL. At higher HBr quantities of 0.050 moles and 0.100 moles, recombination reactions became extreme as the elution volumes observed were even higher than those observed for the starting Kraft lignin.

The results obtained indicated that the molar amount of 0.009 per 2 g of lignin and 0.113 moles of DMSO would be most suitable to effectively cleave lignin to its monomeric and/or oligomeric compounds.

Example VI

Influence of Temperature

While maintaining the quantities of reagents and other reaction conditions used in Example V of Table 7 above, the depolymerisation temperature was systematically varied as tabulated in Table 8.

TABLE 8

Experimental parameters and conditions for study on
influence of varying depolymerisation temperature.

| Reaction | Reagents | Temperature (° C.) |
|---|---|---|
| 7 | Kraft lignin (2 g), DMSO (1.13 × $10^{-1}$ moles), HBr (0.009 moles) | 80 |
| 8 | Kraft lignin (2 g), DMSO (1.13 × $10^{-1}$ moles), HBr (0.009 moles) | 90 |
| 9 | Kraft lignin (2 g), DMSO (1.13 × $10^{-1}$ moles), HBr (0.009 moles) | 110 |
| 10 | Kraft lignin (2 g), DMSO (1.13 × $10^{-1}$ moles), HBr (0.009 moles) | 120 |
| 11 | Kraft lignin (2 g), DMSO (1.13 × $10^{-1}$ moles), HBr (0.009 moles) | 150 |

Figure 4:
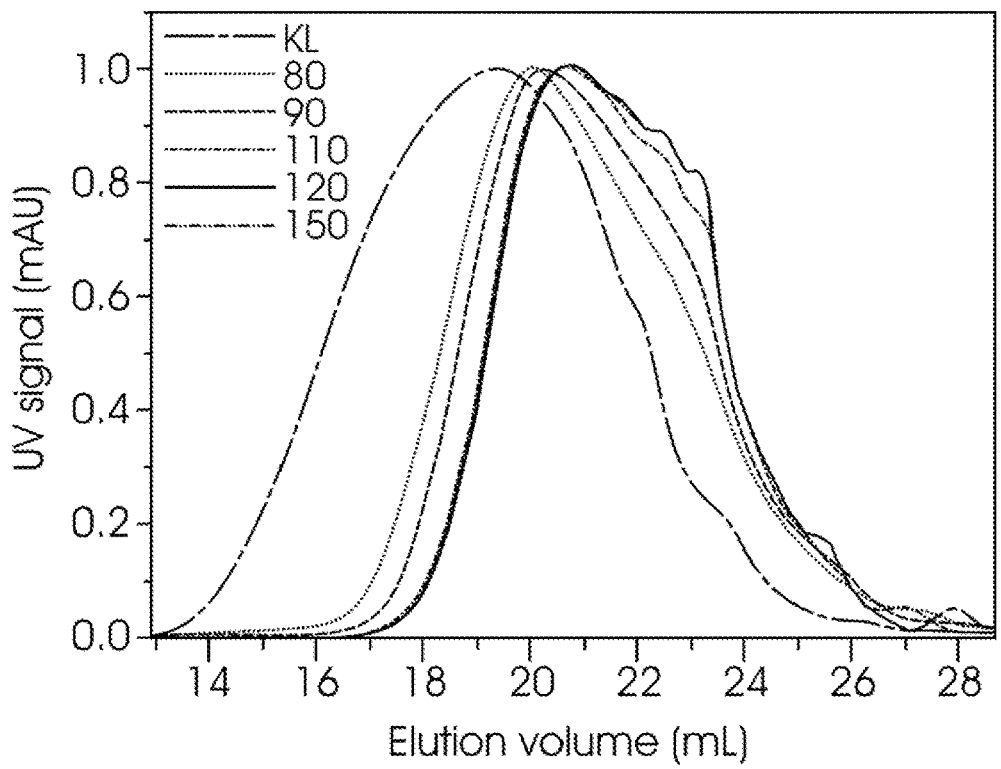
FIG. 4 is a series of SEC elution profiles illustrating the influence of varying depolymerisation temperature.

As in the case of the study relating to HBr concentration, SEC was also used in the temperature study to monitor the success of the depolymerisation reaction, and the results are illustrated in FIG. 4.

Although reaction temperatures of 80° C. and 90° C. already resulted in a shift towards lower molar mass species, the shift became enhanced at higher temperatures of 110° C. and 120° C. However, depolymerising lignin at even higher temperatures such 150° C. became less suitable owing to the bulk formation of char (solid carbonised material), which is insoluble in the mobile phase used for SEC.

Isolation of Reaction Products

The reaction products of the oxidative depolymerisation of lignin were distilled under vacuum and fractions collected at the following temperatures: 100-130° C., 140-150° C., 160° C. and 180° C. After all the fractions were collected they were quantified gravimetrically. The fraction that contained the undistilled product was also quantified gravimetrically. The percentage of recovered sample was calculated according to the following equation:

% of recovered sample=(weight of fraction/weight of crude product mixture)×100% where Weight of fraction is the mass of the recovered fraction at a particular temperature by vacuum distillation of the crude DMSO/HBr product mixture and Weight of crude product mixture is the mass of the crude lignin/DMSO/HBr product mixture before vacuum distillation.

The quantity of material recovered at each temperature is shown in Table 9 below:

TABLE 9

Gravimetric quantification of product fractions
(phase 1 = liquid phase, phase 2 = solid phase)

| Fraction number | Description | Recovered sample (g) | % of recovered sample |
|---|---|---|---|
| 1 | 100-130° C. (phase 1) | 1.84 | 12.3 |
| 2 | 100-130° C. (phase 2) | 2.73 | 18.2 |
| 3 | 140-150° C. (phase 1) | 0.98 | 6.5 |
| 4 | 140-150° C. (phase 2) | 3.84 | 25.6 |
| 5 | 160° C. (phase 1) | 1.56 | 10.4 |
| 6 | 160° C. (phase 2) | 0.42 | 2.8 |
| 7 | 180° C. (phase 1) | 0.96 | 6.4 |
| 8 | 180° C. (phase 2) | 0.44 | 2.9 |
| Undistilled fraction | — | 0.83 | 5.5 |
| Solid char | — | 1.4 | 9.3 |

Analysis of Fraction 140-150° C. (Phase 1)

Syringaldehyde and benzaldehyde were isolated from the 140-150° C. fraction in an amount of 31.1% syringaldehyde and 6.4% benzaldehyde (based on single point calibration) and identified by LC-MS mass spectrometry.

Analysis of 160° C. Fraction (Phase 2)

Eugenol is the compound that was quantified and identified from the 160° C. fraction (phase 2) by LC-MS in positive SIM mode and was quantified at 21.8% (by mass of injected sample) using single point calibration.

Analysis of Fraction 180° C. (Phase 1)

Figure 5:
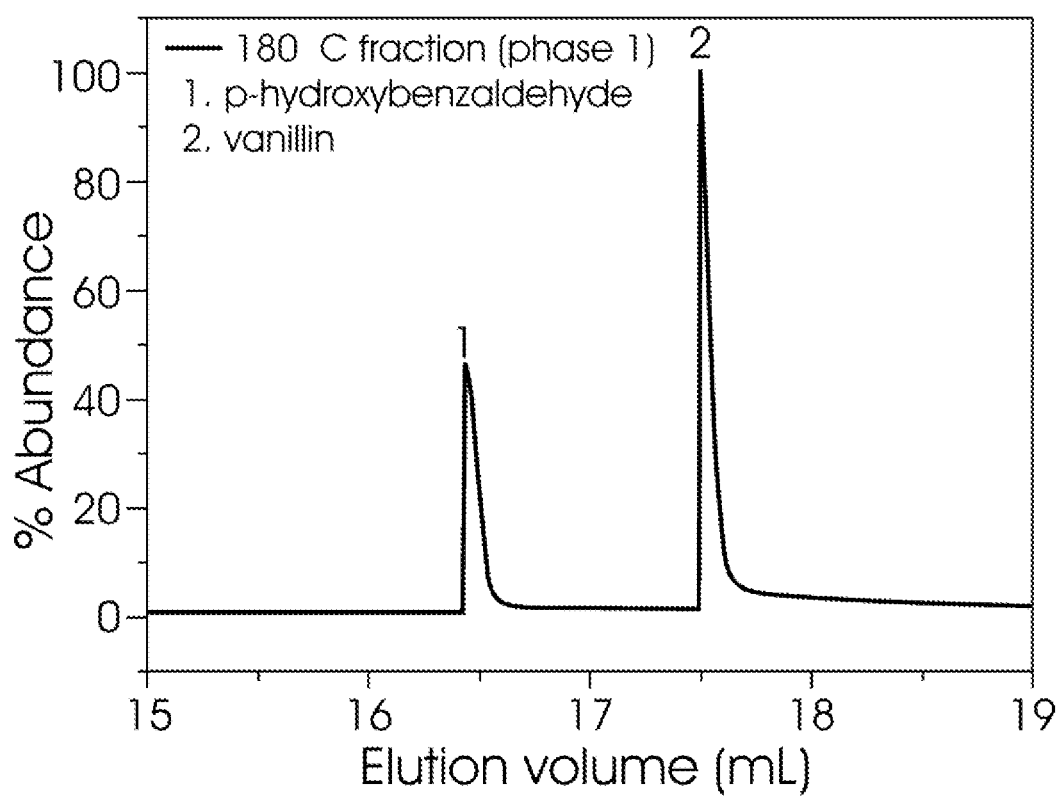
FIG. 5 is a liquid chromatography-mass spectrometry (LC-MS) single ion monitoring (SIM) elugram of a product fraction of an oxidative depolymerisation reaction performed on lignin. The product fraction, isolated by vacuum distillation at 180° C. and approximately 0 kPa, shows peaks for p-hydroxybenzaldehyde and vanillin.

Vanillin ($V_e$: 17.5 mL) and p-hydroxybenzaldehyde ($V_e$: 16.4 mL) were identified from the 180° C. (phase 1) fraction by LC-MS in positive SIM mode. FIG. 5 illustrates the HPLC elugram showing the presence of vanillin and p-hydroxybenzaldehyde. Vanillin is present in an amount of 32.4% (determined by single point calibration) whereas p-hydroxybenzaldehyde is present in an amount of 13.6%.

Undistilled Fraction

Vacuum distillation was carried up to 180° C. and the high boiling point fraction was isolated by decanting from the undistilled fraction. Increasing temperature beyond 180° C. on the undistilled bulk sample led to formation of solid char. The high boiling point fraction was also characterized by LC-MS in SIM mode only. Phloroglucinol ($V_e$: 10.96 mL, 5.5% by mass of injected sample) and 2,4-dihydroxybenzaldehyde ($V_e$: 17.15 mL, 12.3% by mass of injected sample) were identified and quantified in this fraction by single point calibration.

The method described above, and illustrated by the Examples, results in a conversion of approximately 50% of lignin to low molar mass value added compounds, a value which is comparable to other previously reported oxidative depolymerisation procedures (Chem Sus Chem. 2010; 3:719-23, Chemical Reviews. 2018; 118:614-78). With the current conditions, approximately 91% of the depolymerised product could be quantitatively recovered through vacuum distillation and approximately 20% to 25% identified as phenolic-type compounds which included vanillin, syringaldehyde, benzaldehyde, p-hydroxybenzaldehyde, eugenol, phenol, guaiacol, phloroglucinol and 2,4 dihydroxybenzaldehyde. The remaining quantity of recovered product was unidentified but could be other aromatic/non-aromatic compounds that were also formed from the depolymerisation process. Solid char was quantified at approximately 9%. Table 10 below summarises the quantities of selected aromatic compounds from an exemplary run of the depolymerisation process.

TABLE 10

Weight % of monomeric compound

| Quantified lignin monomeric compound | Weight (mg) by single point calibration | % of monomeric compound | % weight of monomer per weight of lignin |
| --- | --- | --- | --- |
| Vanillin | 311.0 | 29.5 | 2.1 |
| Benzaldehyde | 62.7 | 5.9 | 0.4 |
| p-Hydroxybenzaldehyde | 130.6 | 12.3 | 0.9 |
| Syringaldehyde | 304.8 | 28.8 | 2.0 |
| Eugenol | 9.2 | 0.9 | 0.06 |
| Phloroglucinol | 56.7 | 5.4 | 0.4 |
| 2,4-Dihydroxybenzaldehyde | 102.1 | 9.6 | 0.7 |
| Phenol | 59.0 | 5.5 | 0.4 |
| Guaiacol | 22.0 | 2.1 | 0.2 |
| Total quantifiable monomeric compounds | 1058.1 | 100 | |

Some advantages of the present invention may include alleviation of overoxidation of primary alcohols to carboxylic acids as means of forming aldehyde functionalised chemicals from lignin and other polyphenolic polymers, lessening repolymerisation of reaction products to high molar mass polymers, which is prevalent in some oxidative depolymerisation methods. The method may be cheaper and requires a less complicated experimental setup. In certain conditions depolymerisation may use mild pH, temperature and pressure conditions; and larger amounts of aromatic functionalised compounds may be produced, including vanillin, syringaldehyde, benzaldehyde, p-hydroxybenzaldehyde, eugenol, 2,4-dihydroxybenzaldehyde, phenol, guaiacol and phlorogucinol, the latter being a compound that is not widely reported as a product of oxidative depolymerisation.

Furthermore, it will be appreciated that the lignin-derived monomers manufactured by the disclosed methods may be suitable for downstream processing such as polymerisation and/or incorporation into advanced materials or resins. The disclosed methods may accordingly find application in the manufacture of substitutes for certain crude-oil based products.

The invention claimed is:

1. A method for depolymerising a phenolic polymer, the method comprising reacting the phenolic polymer with dimethylsulphoxide and a hydrogen halide, wherein the product of the reaction comprises at least one compound selected from monomeric and oligomeric forms of vanillin, syringaldehyde, benzaldehyde, p-hydroxybenzaldehyde, eugenol, phenol, phloroglucinol, and 2,4-dihydroxybenzaldehyde.

2. The method as claimed in claim 1 wherein the phenolic polymer is lignin.

3. The method as claimed in claim 2, wherein the lignin is selected from kraft lignin, softwood kraft lignin, hardwood kraft lignin, Brauns' lignin, cellulolytic enzyme lignin, dioxane acidolysis lignin, Klason lignin, milled wood lignin, periodate lignin, lignosulphates, lignosulphonates, organosolv lignin, steam explosion lignin, lignocellulosic biomass, lignin residue, and any combination thereof.

4. The method as claimed in claim 1 wherein the hydrogen halide is HBr.

5. The method as claimed in claim 1 wherein the quantity of hydrogen halide per gram of phenolic polymer is from 30 mmoles to 70 mmoles.

6. The method as claimed in claim 1 wherein the quantity of dimethylsulphoxide per gram of phenolic polymer is from 0.1 mole to 1 mole.

7. The method as claimed in claim 1 wherein the reaction is performed at a temperature of from 100° C. to 120° C. for between 10 h and 14 h.

8. The method as claimed in claim 1, which includes isolating a product of the reaction at least in part by vacuum distillation performed at one or more temperatures between 100° C. and 180° C.

9. A method of producing an aromatic compound from a phenolic polymer, the method comprising reacting the phenolic polymer with dimethylsulphoxide and a hydrogen halide to form a reaction mixture, and isolating the aromatic compound from the reaction mixture, wherein the aromatic compound is selected from monomeric and oligomeric forms of vanillin, syringaldehyde, benzaldehyde, p-hydroxybenzaldehyde, eugenol, phenol, phloroglucinol, and 2,4-dihydroxybenzaldehyde.

10. The method as claimed in claim 9 wherein the phenolic polymer is lignin.

11. The method as claimed in claim 10 wherein the lignin is selected from kraft lignin, softwood kraft lignin, hardwood kraft lignin, Brauns' lignin, cellulolytic enzyme lignin, dioxane acidolysis lignin, Klason lignin, milled wood lignin, periodate lignin, lignosulphates, lignosulphonates, organosolv lignin, steam explosion lignin, lignocellulosic biomass, lignin residue, and any combination thereof.

12. The method as claimed in claim 9 wherein the quantity of hydrogen halide per gram of phenolic polymer is from 30 mmoles to 70 mmoles.

13. The method as claimed in claim 9 wherein the hydrogen halide is HBr.

14. The method as claimed in claim 9 wherein the quantity of dimethylsulphoxide per gram of phenolic polymer is from 0.1 mole to 1 mole.

15. The method as claimed in claim 9 wherein the reaction is performed at a temperature of from 100° C. to 120° C. for between 10 h and 14 h.

16. A method of producing vanillin from lignin, the method comprising reacting the lignin with dimethylsulphoxide and a hydrogen halide to form a reaction mixture, and isolating vanillin from the reaction mixture.

17. The method as claimed in claim 16 wherein the quantity of hydrogen halide per gram of lignin is from 30 mmoles to 70 mmoles.

18. The method as claimed in claim 16 wherein the quantity of dimethylsulphoxide per gram of lignin is from 0.1 mole to 1 mole.

19. The method as claimed in claim 16 wherein the hydrogen halide is HBr.

20. The method as claimed in claim 16 wherein the reaction is performed at a temperature of from 100° C. to 120° C. for between 10 h and 14 h.

* * * * *